United States Patent
Gornto

(10) Patent No.: US 11,471,642 B2
(45) Date of Patent: Oct. 18, 2022

(54) PERSONAL THERAPY SYSTEMS AND METHODS EMPLOYING SENSORY STIMULATION

(71) Applicant: Custom Training Solutions LLC, Peru, IN (US)

(72) Inventor: Jason S. Gornto, Peru, IN (US)

(73) Assignee: CUSTOM TRAINING SOLUTIONS LLC, Peru, IN (US)

( * ) Notice: Subject to any disclaimer, the term of this patent is extended or adjusted under 35 U.S.C. 154(b) by 0 days.

(21) Appl. No.: 16/749,085

(22) Filed: Jan. 22, 2020

(65) Prior Publication Data

US 2021/0016051 A1  Jan. 21, 2021

Related U.S. Application Data

(60) Provisional application No. 62/876,066, filed on Jul. 19, 2019.

(51) Int. Cl.
*A61M 21/02* (2006.01)
*A61M 21/00* (2006.01)

(52) U.S. Cl.
CPC ............ *A61M 21/00* (2013.01); *A61M 21/02* (2013.01); *A61M 2021/0016* (2013.01); *A61M 2021/0022* (2013.01); *A61M 2021/0066* (2013.01); *A61M 2205/59* (2013.01)

(58) Field of Classification Search
CPC ....................... A61M 21/00–02; A01K 5/0114
See application file for complete search history.

(56) References Cited

U.S. PATENT DOCUMENTS

| | | |
|---|---|---|
| 4,500,725 A | 2/1985 | Yemoto et al. |
| 4,524,018 A | 6/1985 | Yemoto et al. |
| 4,908,208 A | 3/1990 | Lee et al. |
| 5,008,115 A | 4/1991 | Lee et al. |
| 5,034,222 A | 7/1991 | Kellett et al. |
| 5,071,704 A | 12/1991 | Fischel-Ghodsian |
| 5,130,171 A | 7/1992 | Prud'Homme et al. |
| 5,176,903 A | 1/1993 | Goldberg et al. |
| 5,185,155 A | 2/1993 | Behan et al. |
| 5,234,689 A | 8/1993 | Lindauer et al. |
| 5,324,444 A | 6/1994 | Berry et al. |
| 5,372,806 A | 12/1994 | Holloway |
| 5,387,411 A | 2/1995 | Abrutyn et al. |
| 5,387,622 A | 2/1995 | Yamamoto |
| 5,490,982 A | 2/1996 | Siciliano |
| 5,500,223 A | 3/1996 | Behan et al. |
| 5,525,555 A | 6/1996 | Zank |
| 5,525,588 A | 6/1996 | Michetti |
| 6,054,547 A | 4/2000 | Perry et al. |
| 6,063,365 A | 5/2000 | Shefer et al. |
| 6,309,715 B1 | 10/2001 | Lindauer et al. |

(Continued)

*Primary Examiner* — Thaddeus B Cox
(74) *Attorney, Agent, or Firm* — Brannon Sowers & Cracraft PC

(57) ABSTRACT

A personal therapy system includes a sensory stimulation pack having a heating device and/or a scent-emitting device, and a holder including a holder body receiving the sensory stimulation pack within a cavity. The holder body has two disc-shaped body pieces releasably attachable to contain the sensory stimulation pack, and vents for outputting heat or scent from the cavity. Surfaces of the holder body have selectively smooth or not smooth textures for varied tactile stimulation of a user.

18 Claims, 16 Drawing Sheets

(56) References Cited

U.S. PATENT DOCUMENTS

| | | | | |
|---|---|---|---|---|
| 6,314,911 B1* | 11/2001 | Kaytovich | | A01K 5/0114 |
| | | | | 119/61.5 |
| 6,938,832 B2 | 9/2005 | Sada | | |
| 7,926,450 B1* | 4/2011 | Tsengas | | A01K 15/025 |
| | | | | 119/711 |
| 8,784,747 B2 | 7/2014 | Carmichael et al. | | |
| 9,610,375 B2* | 4/2017 | Zhang | | A61L 9/12 |
| 10,925,459 B2* | 2/2021 | Shin | | A47L 15/42 |
| 2004/0068781 A1* | 4/2004 | Hill | | A61L 9/02 |
| | | | | 4/222 |
| 2004/0235430 A1 | 11/2004 | Ma et al. | | |
| 2007/0098148 A1 | 5/2007 | Sherman | | |
| 2008/0313789 A1 | 12/2008 | Manne | | |
| 2009/0260393 A1* | 10/2009 | Robbins-Sullivan | | A61L 9/12 |
| | | | | 63/1.15 |
| 2010/0281928 A1* | 11/2010 | Martin | | D06F 39/024 |
| | | | | 68/213 |
| 2011/0198409 A1* | 8/2011 | Gorman | | A47G 33/0854 |
| | | | | 239/34 |
| 2012/0061486 A1* | 3/2012 | Atkinson | | A61L 9/127 |
| | | | | 239/34 |
| 2014/0076989 A1* | 3/2014 | Granger | | A61L 9/12 |
| | | | | 239/52 |
| 2014/0193764 A1* | 7/2014 | Pizzini | | A61M 15/08 |
| | | | | 432/247 |
| 2015/0014429 A1* | 1/2015 | Rome | | A61M 15/08 |
| | | | | 239/6 |
| 2017/0127647 A1* | 5/2017 | Owens, III | | A01K 5/0114 |
| 2018/0311394 A1* | 11/2018 | Cutler | | A61L 9/12 |
| 2018/0333336 A1* | 11/2018 | Walker | | A61J 17/109 |
| 2018/0352784 A1* | 12/2018 | Theno | | A01K 13/003 |
| 2019/0168240 A1* | 6/2019 | Beesley | | A61L 9/03 |
| 2019/0298618 A1* | 10/2019 | Becker | | A61J 17/00 |

\* cited by examiner

PERSONAL THERAPY SYSTEMS AND METHODS EMPLOYING SENSORY STIMULATION

TECHNICAL FIELD

The present disclosure relates generally to a personal therapy system and, more particularly, to a personal therapy system having a holder specialized with tactile stimulation surfaces and containing a sensory stimulation pack.

BACKGROUND

A great many different personal therapy devices are used at home and in institutional settings. Heating pads, massagers, white noise machines, scent-emitting devices and various others are well known, and widely used. Such devices and strategies typically focus on stimulating a single sensory modality. U.S. Pat. No. 8,784,747 to Carmichael et al. is directed to a Fragrance Dispenser for Use With Portable Electronic Device. Carmichael et al. propose a cover for holding and protecting a scent insert for use with a portable electronic device. Apparently, the aromatic insert is scent impregnated, and a pocket in a cover for the electronic device is porous or includes apertures for transferring scent outside of a pocket insert holder. Other devices and systems are known that attempt to combine sound with scent, heat with tactile stimulation, or other combinations of sensory stimulatory pathways. With increased awareness of the need for treating physical infirmities as well as various psychological or mental conditions, the field welcomes improvements and alternative strategies.

SUMMARY OF THE INVENTION

In one aspect, a personal therapy system includes a sensory stimulation pack including at least one of a heating device or a scent-emitting device. The system further includes a holder having a holder body defining a center axis and having a first disc-shaped body piece, and a second disc-shaped body piece releasably attached to the first disc-shaped body piece. The first disc-shaped body piece and the second disc-shaped body piece each include a body wall having an inner surface, and an outer surface, the inner surfaces forming a cavity receiving the sensory stimulation pack. The first disc-shaped body piece has a plurality of vents formed in the body wall thereof, for outputting heat or scent from the cavity produced, respectively, by the at least one of a heating device or a scent-emitting device. The outer surface of the first disc-shaped body piece forms a first outer touch surface having a smooth texture throughout and extending radially outward of, and circumferentially around, the center axis. The first disc-shaped body piece further includes an outer peripheral wall depending axially downward from the body wall thereof, and the outer peripheral wall including a peripheral surface forming a second outer touch surface. The second outer touch surface has a not smooth texture throughout and extends, at a uniform radial distance, circumferentially around the center axis.

DETAILED DESCRIPTION

Figure 1:
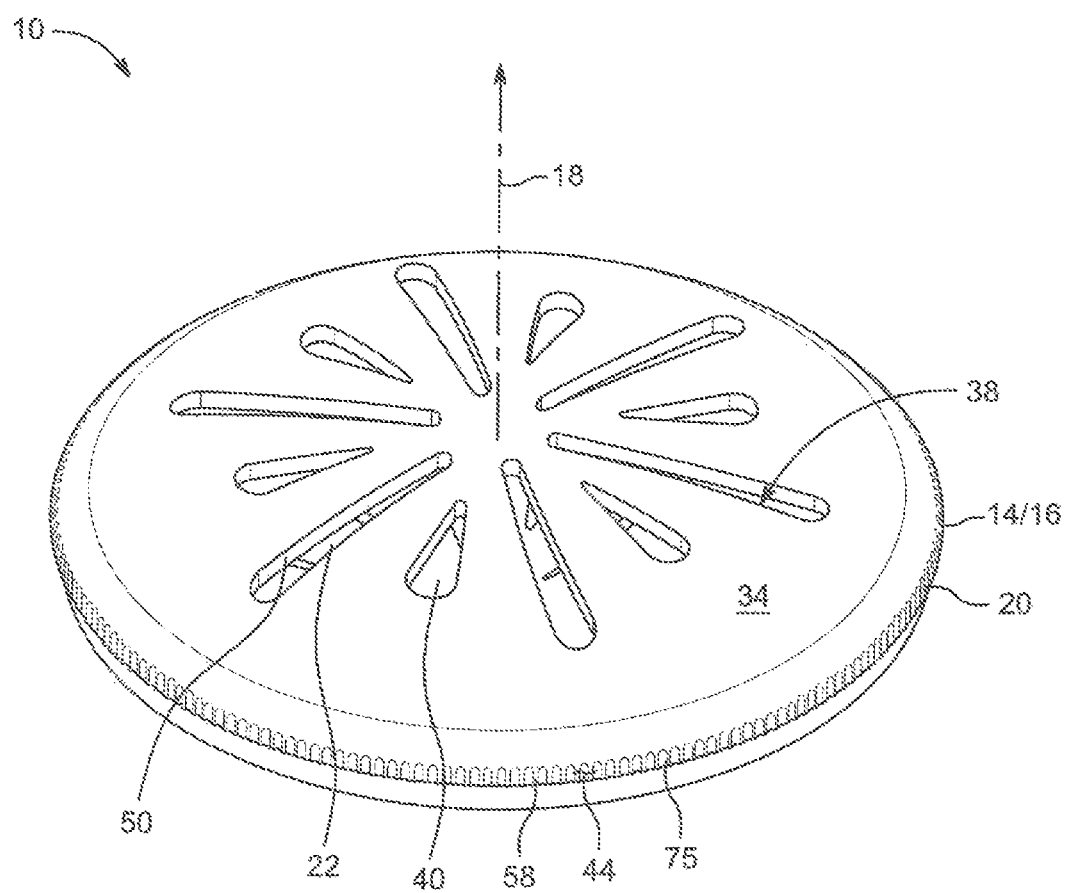
FIG. 1 is a perspective view of a personal therapy system, according to one embodiment.
Figure 2:
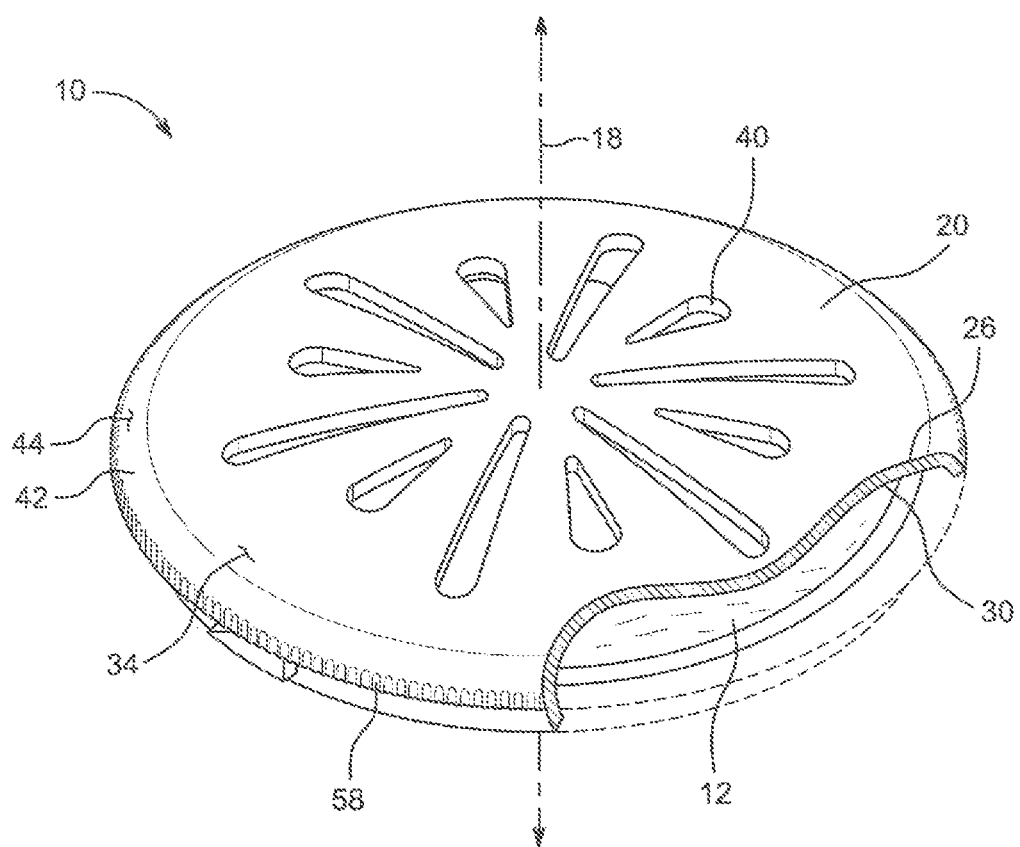
FIG. 2 is a perspective view, in partial cutaway, of parts of the system of FIG. 1.
Figure 3:
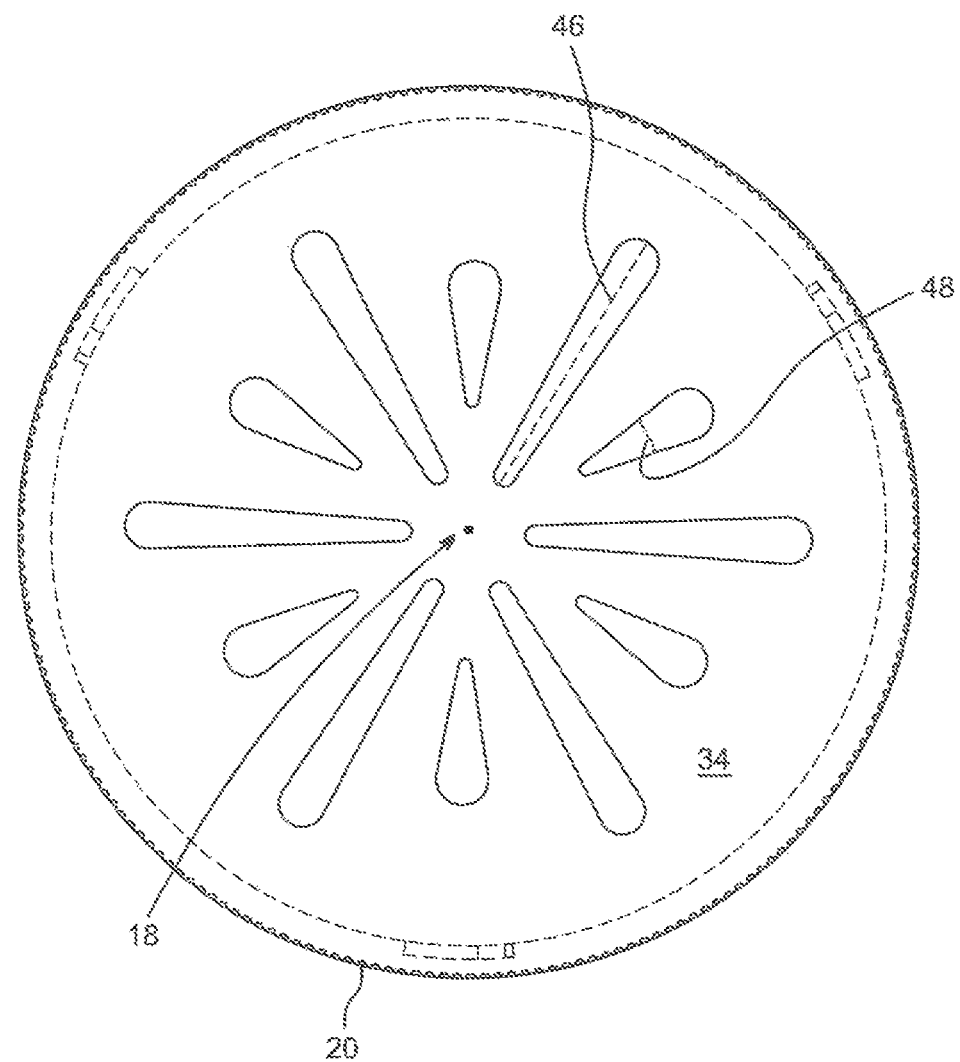
FIG. 3 is a top view of a body piece in the system of FIG. 1.

Referring to FIG. 1, there is shown a personal therapy system 10 according to one embodiment. Personal therapy system 10 is structured for containing at least one of a heating device or a scent-emitting device in a sensory stimulation pack, and is further structured with surface features and texturing for tactile stimulation of a user. It is contemplated personal therapy system 10 can be used as a massage device, or more generally for any tactile stimulation of the body of a user including, but not limited to, a user's head, torso, arms, legs, hands or feet. A user can manually manipulate personal therapy system 10 on an ad hoc basis as desired, or according to any of a variety of prescribed techniques. Personal therapy system 10 could be used, for example, by advancing along or across a users face, neck, et cetera to simultaneously produce tactile stimulation, olfactory stimulation, and temperature stimulation.

In some instances, personal therapy system 10 produces both heat and scent, such as by positioning a hot pack component and a scent-emitting component together in a cooperative fashion so that the heat initiates or increases the production of scent vapor. One example heating device includes a so-called super-cooled sodium acetate disc. A flexible metallic initiator can be positioned inside the sodium acetate disc, or within packaging for the sodium acetate disc, and actuated in a generally known manner to induce a chemical reaction or physical change to produce heat. Such a heating device can be relatively small, for instance only a few centimeters in diameter. Other heating devices can include granulated or powdered iron-based heating devices, a heat holding device that is energized by heating in a microwave or the like and then discharges, or still others. An example scent-emitting device can include a cloth device or another fibrous device, a sponge, or any of a variety of other commercially available scent-emitting devices that can be selectively infused or soaked with an essential oil that is plant derived, or still another material. As noted above, the heat and scent devices can operate cooperatively. In still other instances, rather than a heating device, a temperature stimulation device in the nature of a cooling device operated on the basis of endothermic chemical reaction, or by precooling, could also be used. It is further contemplated that a user might use personal therapy system 10 for parts of the user's body that are injured or otherwise infirm, however, the present disclosure is also not limited in this regard.

Referring also now to FIGS. 2-10, personal therapy system 10 can include a sensory stimulation pack 12 as discussed above structured to stimulate multiple sensory modalities of a user. Personal therapy system 10 also includes a holder 14 having a holder body 16 defining a center axis 18, and having a first disc-shaped body piece 20, and a second disc-shaped body piece 22 releasably attached to the first disc-shaped body piece. The first and the second disc-shaped body pieces 20 and 22 each include a body wall 26 and 28, respectively. Body wall 26 has an inner surface 30, and body wall 28 has an inner surface 32. Each of first and second disc-shaped body pieces 20 and 22 also includes an outer surface 34 and 36, respectively, formed on the corresponding body wall 26 or 28. Inner surfaces 30 and 32 form a cavity 38 structured to receive sensory stimulation pack 12.

First disc-shaped body piece 20 also has a plurality of vents 40 formed in body wall 26, for outputting heat or scent from cavity 38 produced, respectively, by at least one of the heating device or scent-emitting device of sensory stimulation pack 12. In the illustrated embodiment vents 40 each define a major axis 46 extending radially outward of center axis 18, and a minor axis 48. Vents 40 may include at least two different vent shapes, and in the illustrated embodiment include vents having diameters increased in a radially outward direction, in two different vent shapes that alternate with one another circumferentially around center axis 18.

Figure 8:
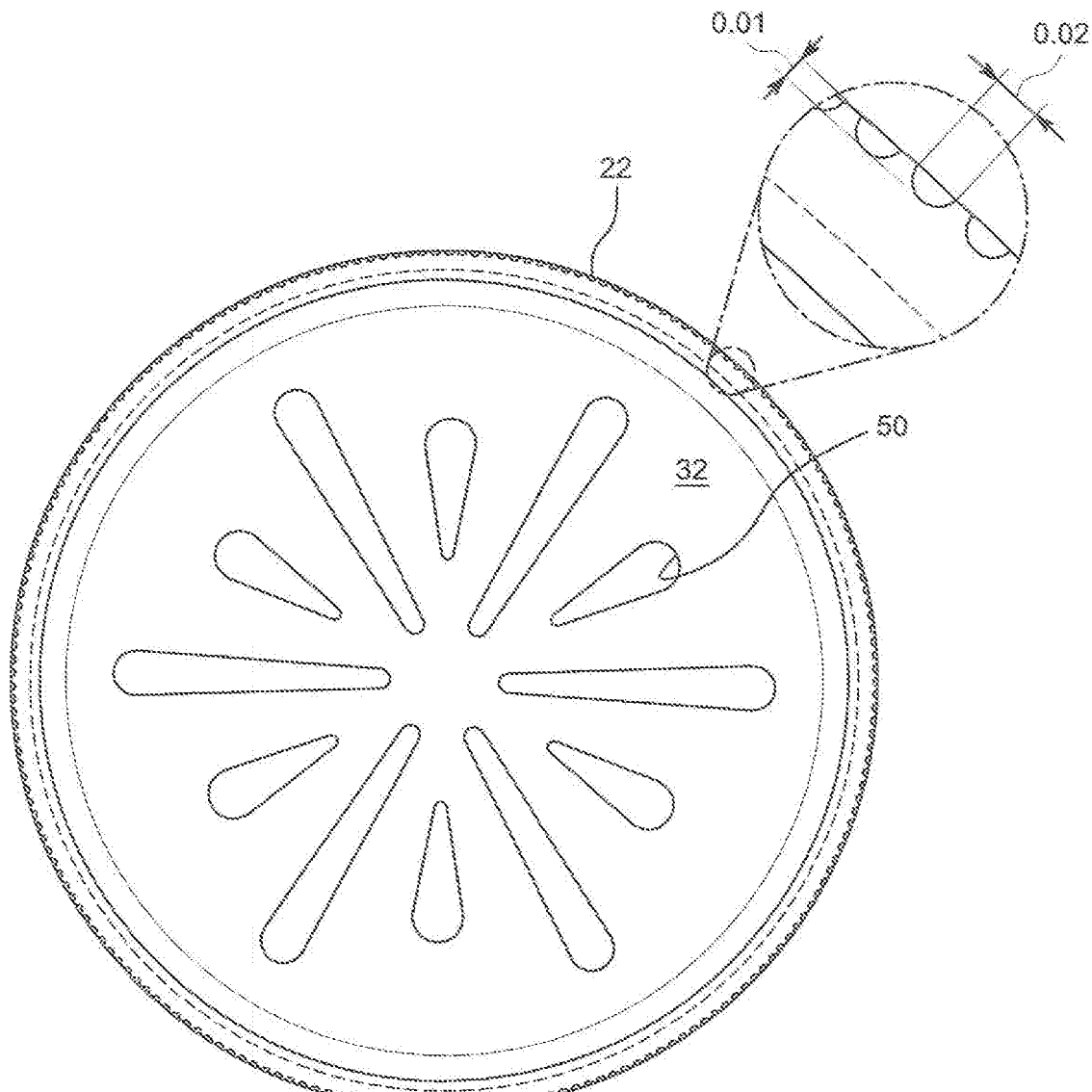
FIG. 8 is a top view of the body piece of FIG. 7, including a detailed enlargement.

Outer surface 34 of first disc-shaped body piece 20 forms a first outer touch surface. The first outer touch surface, which may be coextensive with outer surface 34 itself, has a smooth texture throughout and extends radially outward of, and circumferentially around, center axis 18. First disc-shaped body piece 20 further includes an outer peripheral wall 42 depending axially downward, or upward depending upon present perspective, from body wall 26. Second disc-shaped body piece 22 may include an outer peripheral wall 33 that depends axially downward, or upward depending upon present perspective, from body wall 28. Outer peripheral wall 42 also includes a peripheral surface 44 forming a second outer touch surface, which may be coextensive with peripheral surface 44 itself. The second outer touch surface has a not smooth texture throughout and extends, at a uniform radial distance, circumferentially around center axis 18. FIG. 8 includes a detailed enlargement showing example dimensions, in inches of a groove in peripheral surface 44 that forms an example of the not smooth texture contemplated herein. As used herein the reference to "first" or "second" in respect of any particular part or feature is not to be understood in a limiting sense. In other words, depending upon perspective a "first" body piece might alternatively be understood as a "second" body piece. Moreover, the smooth texture of the first outer touch surface need not be completely or microscopically smooth, but is understood in comparative relation to the disclosed not smooth texture. Surfaces described as having a smooth texture may have a texture imparted by molding apparatus by which the part is made, although coatings or finishing procedures might produce a different texture. The not smooth texture may be analogously produced, and will typically include ribs, grooves, scoring, flutes, ridges, application of a gritty coating, or any of a variety of other three-dimensional features, the significance of which will be further apparent from the following description.

In the illustrated embodiment, body wall 26 of first disc-shaped body piece 20 has a dome shape, as depicted in the drawings. Body wall 28 of second disc-shaped body piece 22 may also have a dome shape, as depicted in the drawings. It will also be understood that first disc-shaped body piece 20 and second disc-shaped body piece 22 are generally complementary, in that second disc-shaped body piece includes outer peripheral wall 44 which is received within outer peripheral wall 42. Any of a variety of other coupling and attachment arrangements could be employed, however, an annular wall within another annular wall is contemplated to be a practical implementation strategy. Second disc-shaped body piece 22 may have another plurality of vents 50 formed therein. Vents 50 could register with vents 40, and have substantially identical shapes, sizes, and configurations. In other instances, vents 40 and 50 might be configured similarly but indexed relative to one another, such that no clear line of sight would extend axially through holder 14, for example. In still other instances, rather than dome shapes, body wall 26 and body wall 28 might be planar, or one of the body walls could be planar and the other dome shaped.

System 10 may further include a twist lock 52 releasably attaching first disc-shaped body piece 20 to second disc-shaped body piece 22. Twist lock 52 can include a first locking element 54 formed on first disc-shaped body piece 20, in particular on outer peripheral wall 42, and a second locking element 56 formed on second disc-shaped body piece 22, in particular on outer peripheral wall 43. First disc-shaped body piece 20 and second disc-shaped body piece 22 are rotatable relative to one another about center axis 18 between a locking state, where first locking element 54 is in locking engagement with second locking element 56, and a release state. Accordingly, holder 14 can be disassembled for placement of sensory stimulation pack 12 therein by rotating body piece 20 and 22, and then pulling the body pieces apart, inserting pack 12, fitting the body pieces back together, and rotating back to a locking state.

Figure 4:
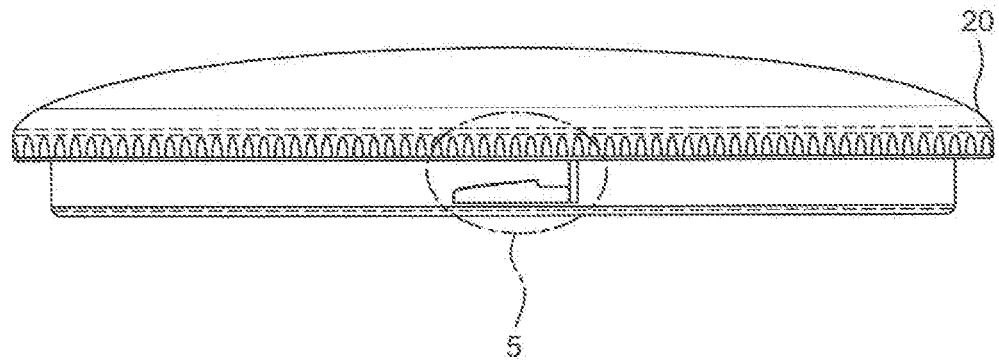
FIG. 4 is a side view of the body piece of FIG. 3.
Figure 5:
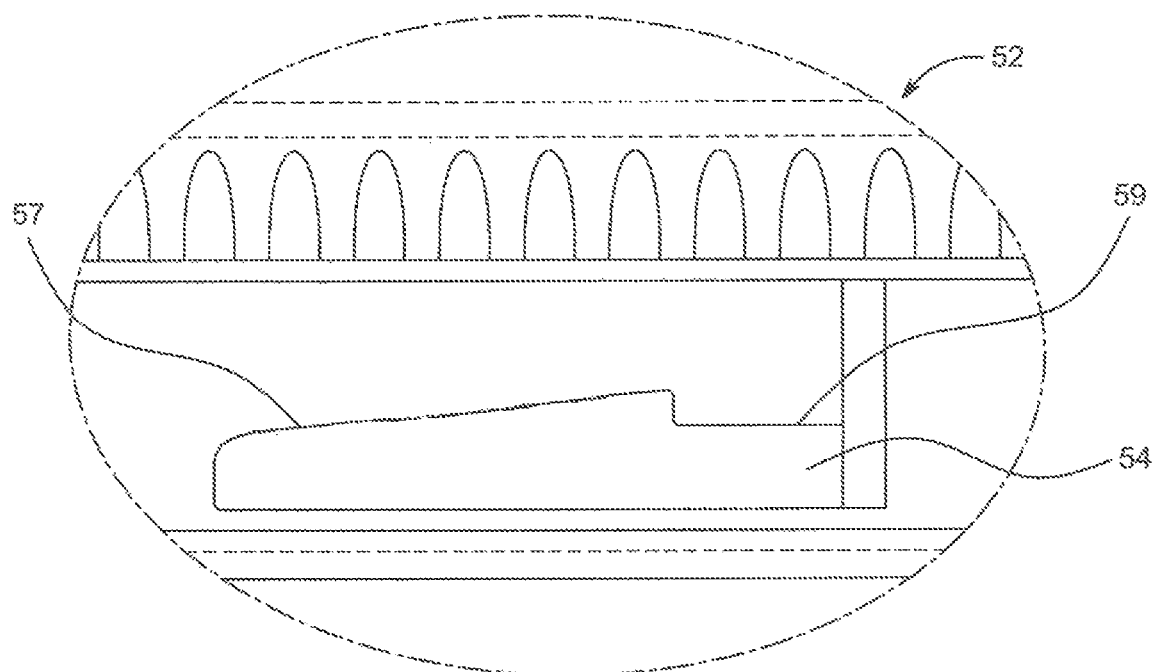
FIG. 5 is a detailed enlargement of a portion of the body piece of FIG. 4.
Figure 6:
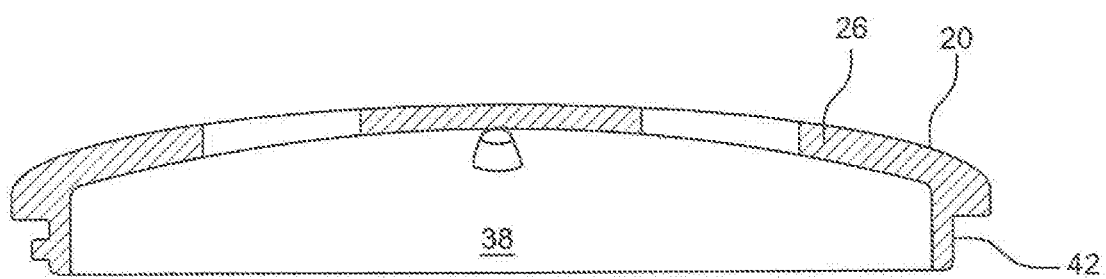
FIG. 6 is a sectioned side diagrammatic view of the body piece of FIGS. 3-4.
Figure 7:
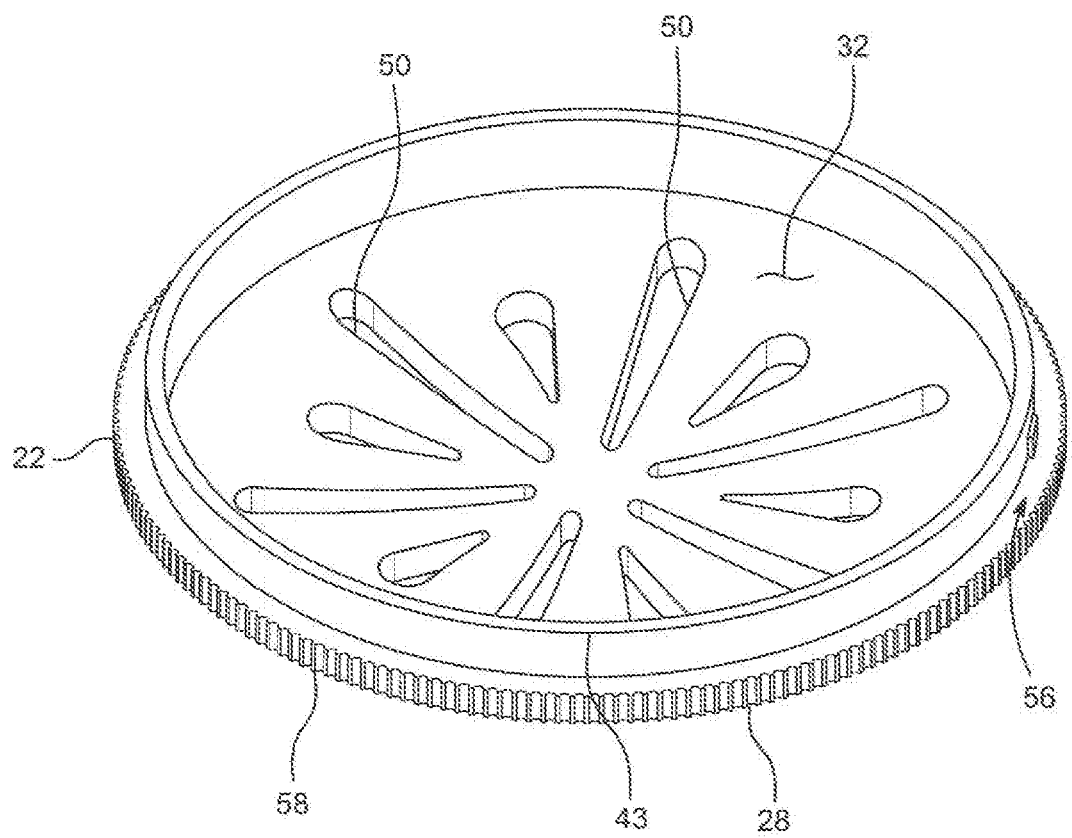
FIG. 7 is a perspective view of another body piece in the system of FIG. 1.
Figure 9:
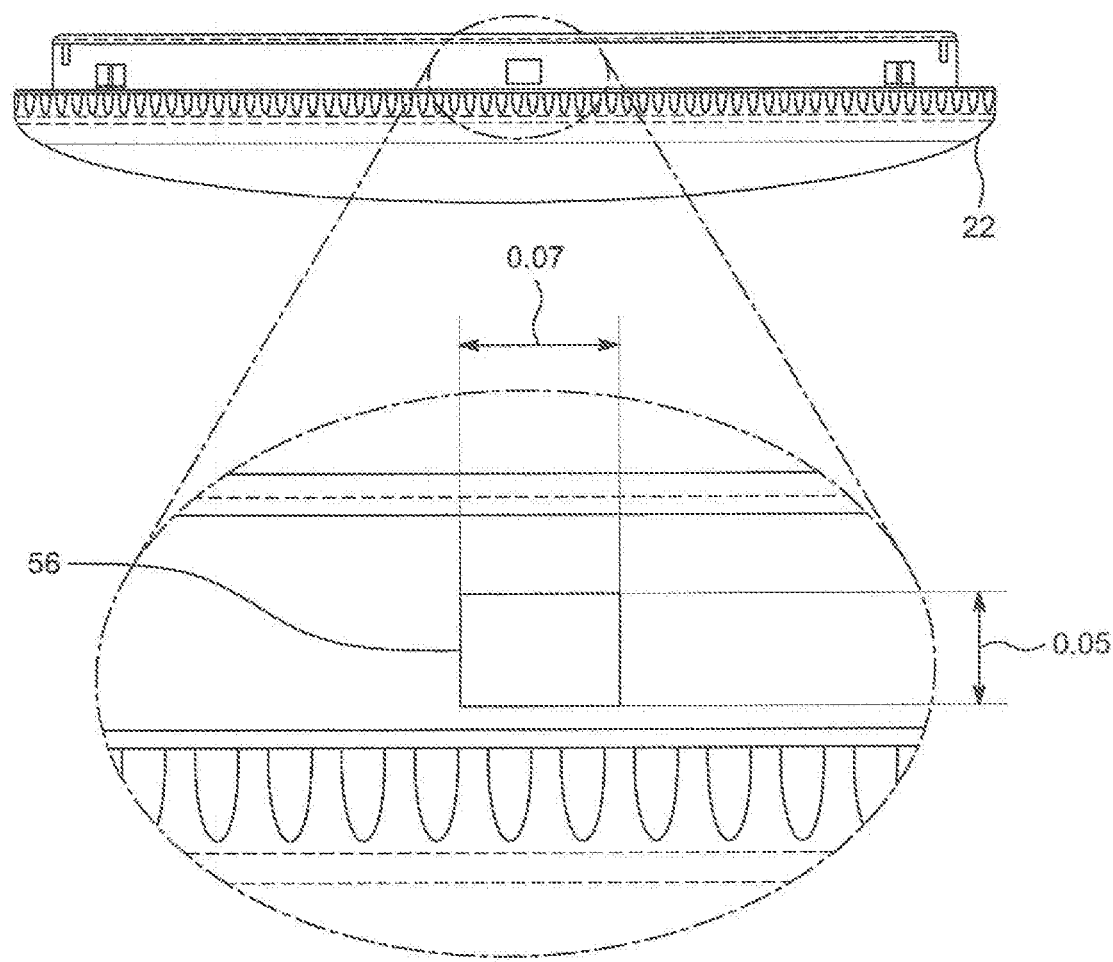
FIG. 9 is a side view of the body piece of FIGS. 7 and 8, including a detailed enlargement.
Figure 10:
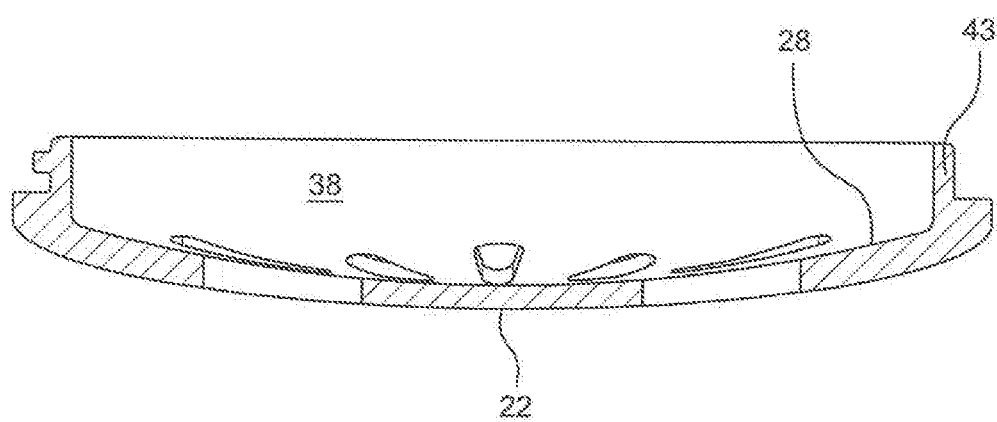
FIG. 10 is a sectioned side diagrammatic view of the body piece of FIGS. 7-9.
Figure 11:
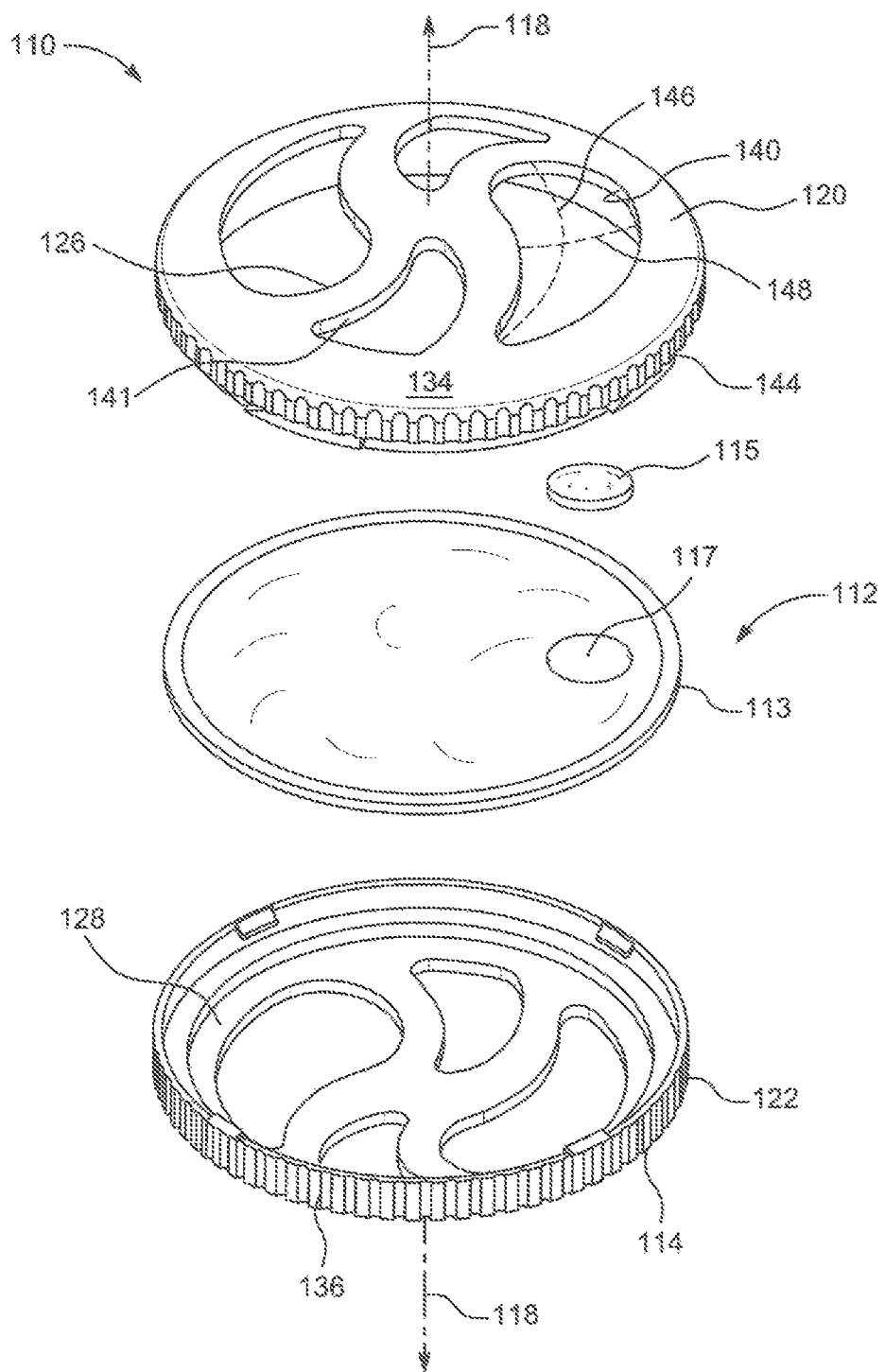
FIG. 11 is an exploded view of a personal therapy system, according to one embodiment.

FIG. 5 includes a detailed enlargement from FIG. 4 at circle 5 illustrating one example locking element configuration of locking element 54 that might be used in conjunction with a locking element configuration of locking element 56. FIG. 9 includes a detailed enlargement, with example dimensions in inches of locking element 56. As depicted in FIG. 5 and FIG. 9, for example, twisting of body pieces 20 and 22, relative to one another, can cause locking element 56 to encounter a ramp 57 of locking element 54, slide against ramp and snap into place within a sot 59 of locking element 54 to releasably lock body pieces 20 and 22 together. In alternative embodiments, a threaded connection, or a frictional engagement alone, between body pieces 20 and 22 might be used, or still another strategy for coupling body pieces 20 and 22 that does not require twisting at all. Each of body pieces 20 and 22 may be formed of a molded polymeric material, with the not smooth texture and the smooth texture each including molded surface features, or the lack of molded surface features, produced in the molding process. It can also be noted that the not smooth texture may be formed in part by each of the outer peripheral surfaces of each of body pieces 20 and 22, which abut one another at a splitline 75.

Referring now to FIGS. 11-19, there is shown a personal therapy system 110 according to another embodiment, having similarities with the previously described embodiment but certain differences. It should be appreciated that discussion and illustration of any one embodiment, according to the present disclosure, is understood to refer by way of analogy to any other embodiments, except where otherwise indicated or apparent from the context. Personal therapy system 110 includes a sensory stimulation pack 112 including at least one of a heating device 113 or a scent-emitting device 115, generally configured analogously to foregoing embodiments. A metallic initiator is shown at 117, sealed inside an envelope of heating device 113 filled with super-cooled liquid sodium acetate solution, for example. Personal therapy system 110 also includes a holder 114 having a holder body 116 defining a center axis 118. Holder body 116 includes a first disc-shaped body piece 20 and a second disc-shaped body piece 22 releasably attached to first disc-shaped body piece 20. First disc-shaped body piece 20 and second disc-shaped body piece 122 each include a body wall 126 and 128, respectively, having an outer surface 134 and 136. A cavity 138 is formed by first disc-shaped body piece 120 and second disc-shaped body piece 122 and is structured to receive sensory stimulation pack 112.

First disc-shaped body piece 120 further has a plurality of vents formed therein, including first vents 140 having a first configuration and second vents 141 having a second configuration different from the first configuration. Second disc-shaped body piece 122 may analogously have vents shaped similarly or identically to vents 140 and vents 141, and registering therewith, or offset from vents 140 and vents 141 when holder 114 is assembled. Each of vents 140 defines a major axis 146 and a minor axis 148. Minor axis 146 may have a curvilinear path forming an arc segment or other curvilinear form about center axis 118. In the illustrated embodiment each of vents 140 has a curved teardrop shape, extending between a head end and a tail end of the respective vents. It is believed that the curved teardrop shape, or other curved shapes, can allow a user to interact with personal therapy system 110 by tactile recognition of a circumferential directional pattern formed by vents 140 and vents 141. In other words, a user can place one or more of their fingers into and through vents 140 and 141 and will sense personal therapy system 110 as having a natural direction of rotation, such as for fidgeting or other handling. It is also intended that the size and shape of vents 140 and 141 can enable users to place their fingers, for example, in direct contact with sensory stimulation pack 112 to experience heat or cold produced by device 113. In this sense, personal therapy system 110 gives a user additional dimensions of interaction with holder 114 in comparison with holder 14 discussed above which may be interpreted not to have a natural direction of rotation, nor permit a user to directly touch a sensory stimulation pack positioned therein.

Figure 12:
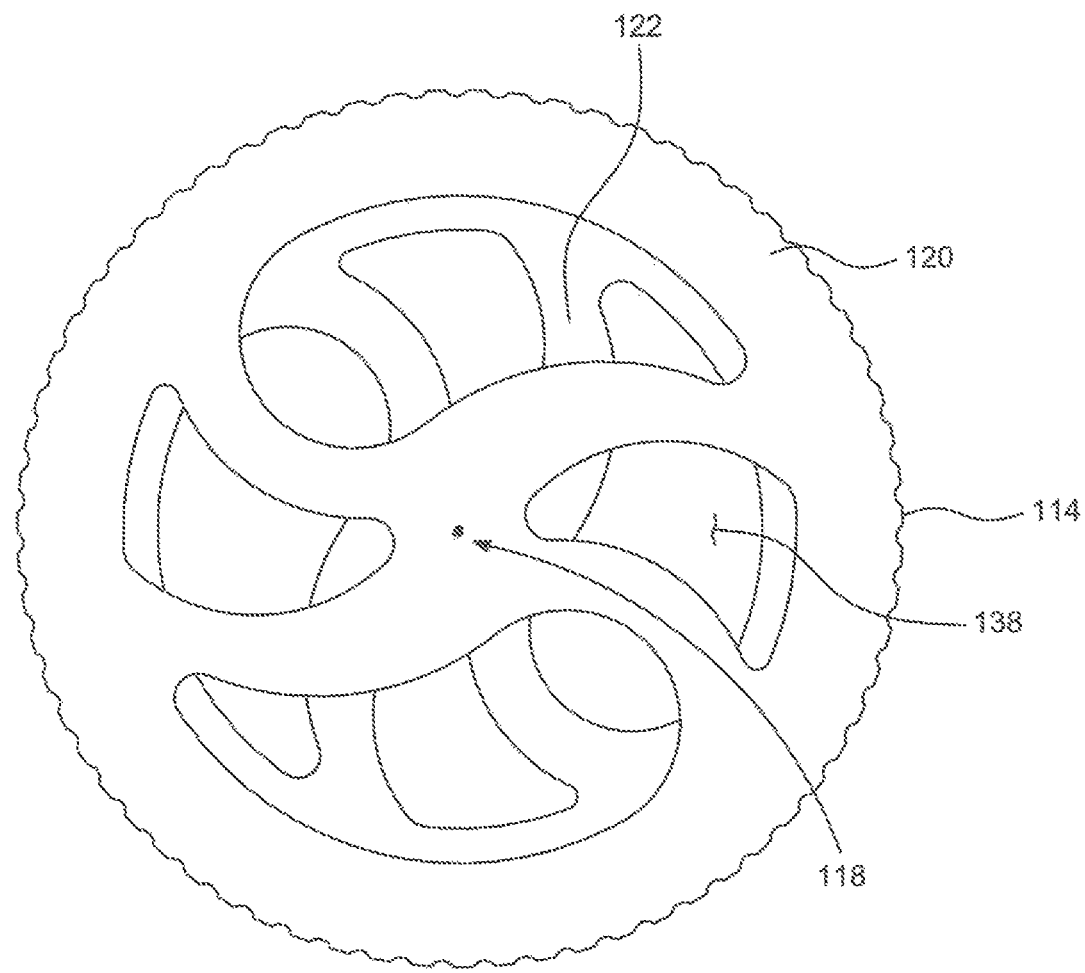
FIG. 12 is a top view of an assembly of parts of a holder for the system of FIG. 11.
Figure 13:
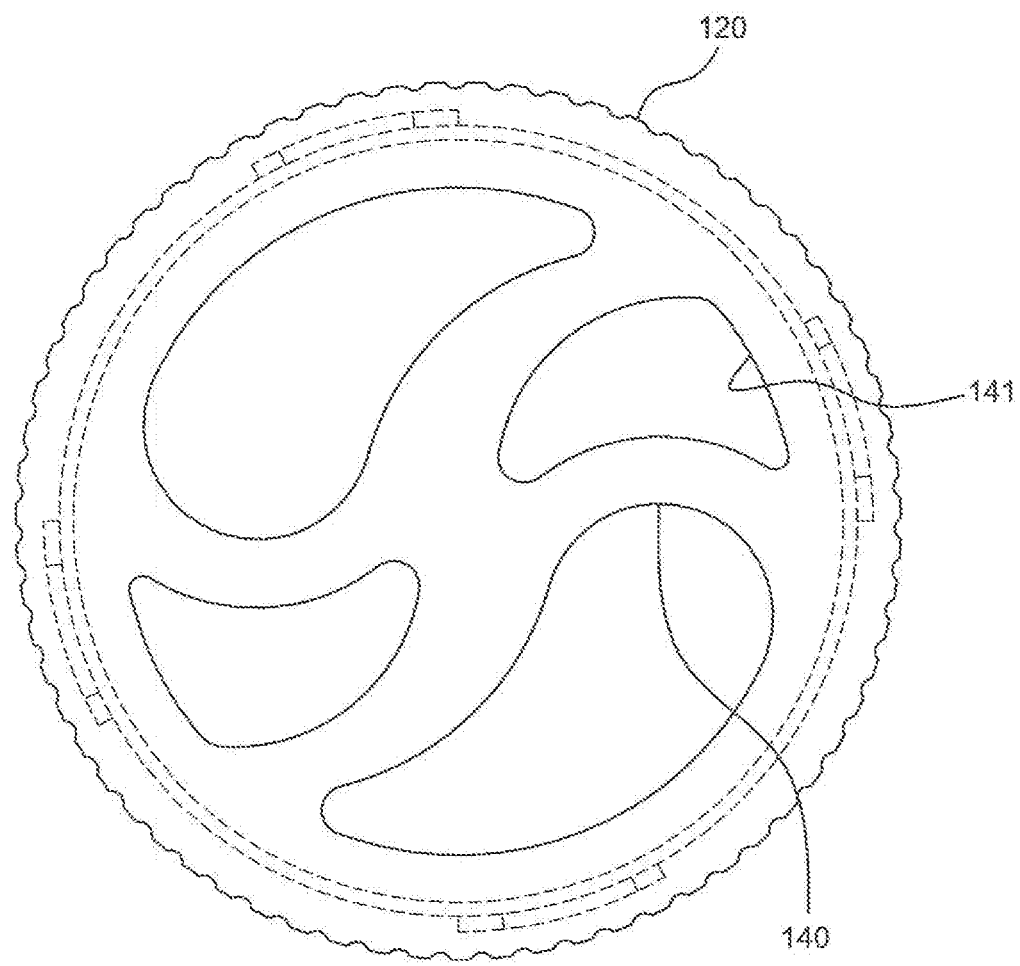
FIG. 13 is a top view of a body piece in the system of FIG. 11.
Figure 14:
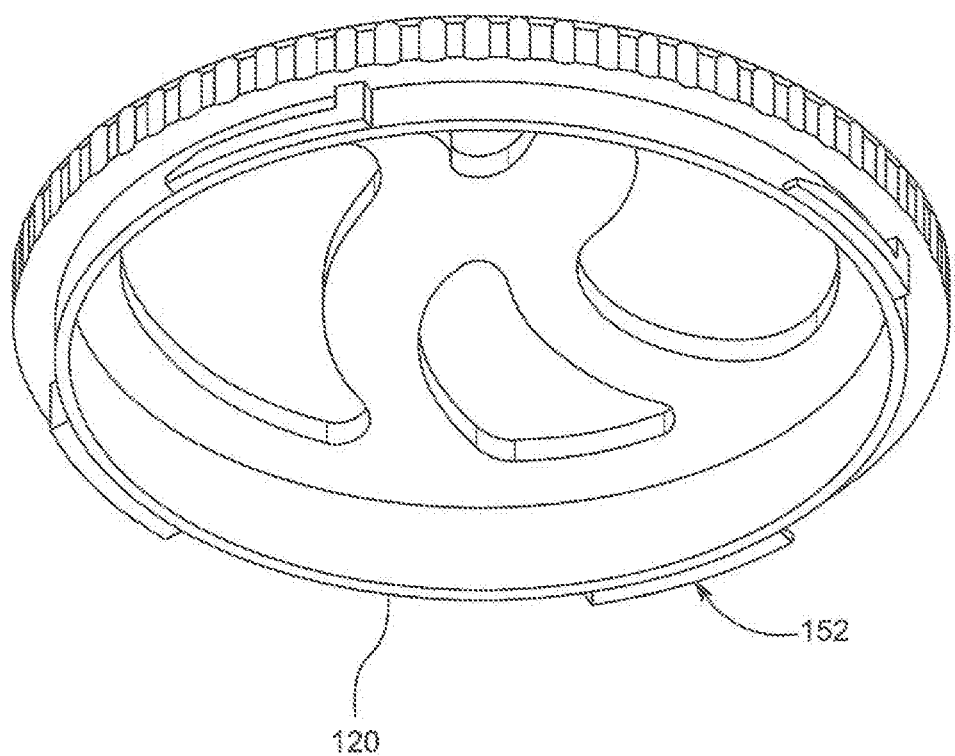
FIG. 14 is a perspective view of the body piece of FIG. 13.
Figure 15:
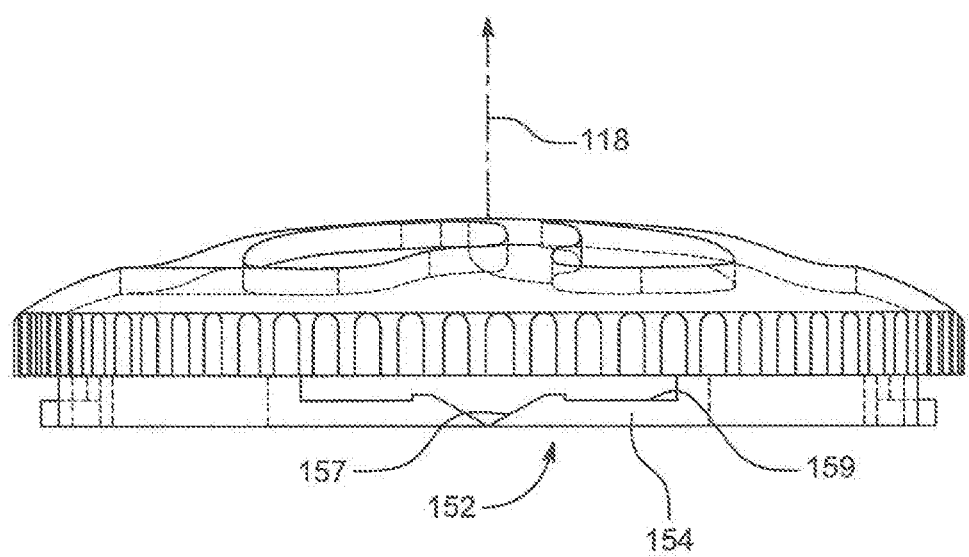
FIG. 15 is a sideview of the body piece of FIG. 13.

FIG. 12 illustrates holder 114 as it might appear having body piece 120 and body piece 122 releasably attached, but where sensory stimulation pack 112 is not captured therein. It can be seen that a clear and direct line of sight can extend through the respective vents in body piece 120 and body piece 122, and also that the respective vents are circumferentially offset from one another. FIGS. 13-15 illustrate top, perspective, and side views of first disc-shaped body piece 120 and illustrating further features thereof, including elements of a twist lock 152. As best depicted in FIG. 15, twist lock 152 includes a locking element 154 having a ramp 157 and a slot 159. Locking element 152 could be bi-directional, with two ramps generally in opposition and two slots adjacent to the respective ramps, approximately as shown, enabling a counterpart locking element 156 on second disc-shaped body piece 122 to engage with locking element 154 by way of rotation in either of two directions about center axis 118.

Figure 16:
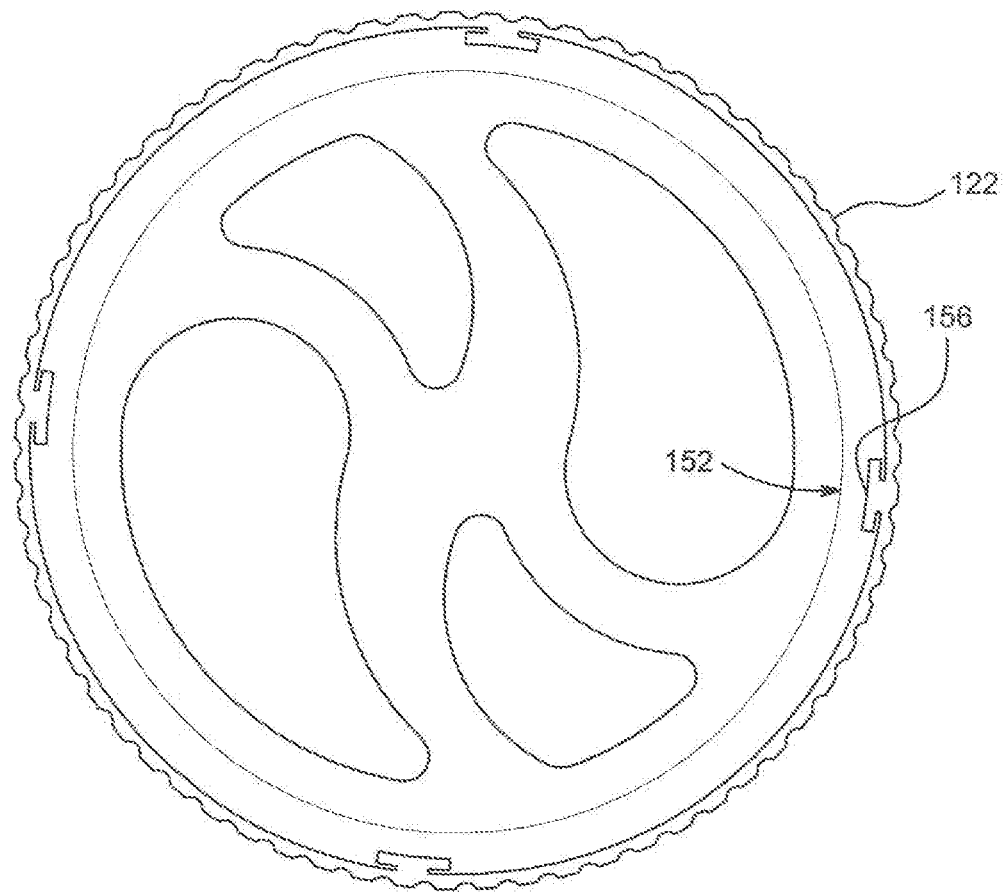
FIG. 16 is a top view of a body piece in the system of FIG. 11.
Figure 17:
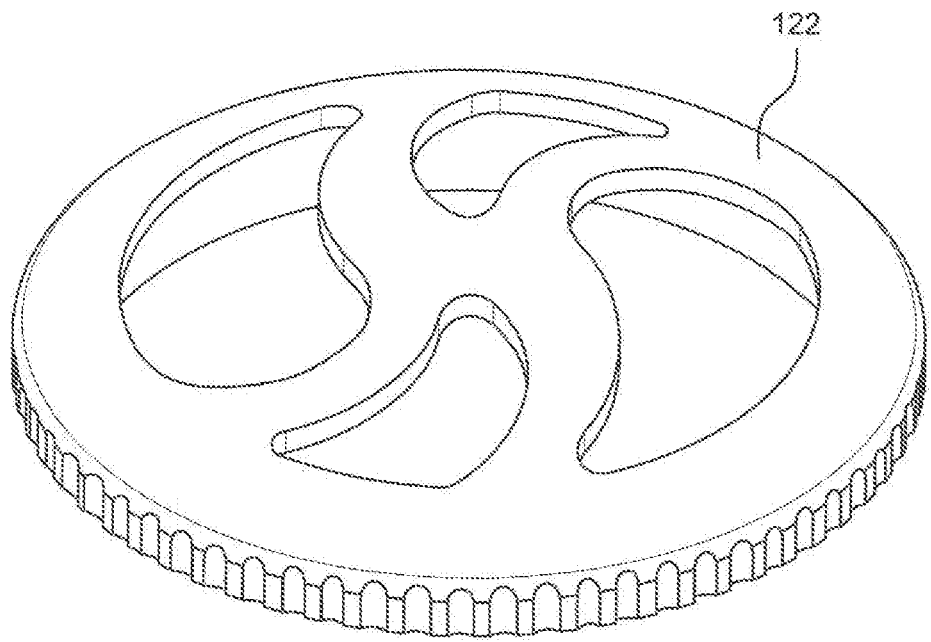
FIG. 17 is a perspective view of the body piece of FIG. 16.
Figure 18:
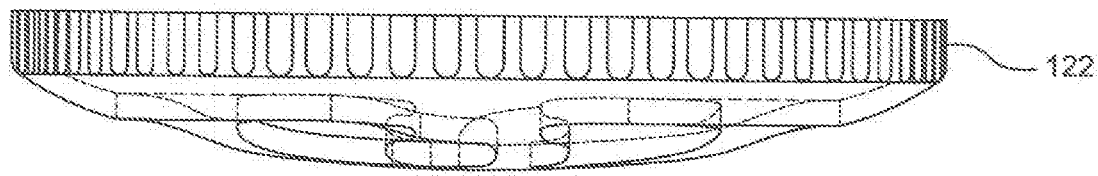
FIG. 18 is a side view of the body piece of FIG. 16.

FIGS. 16-18 illustrates top, perspective, and side views of second disc-shaped body piece 122. It can be seen that locking element 156 of twist lock 152 that is formed on second disc-shaped body piece 122 can be structured to engage with locking element 154 by way of rotation in either of two directions about center axis 118. Although not specifically described, holder 114 may be structured analogously to holder 14 discussed above with respect to tactile stimulation features, including a smooth texture on outer surfaces 134 and 136 of first disc-shaped body piece 120 and second disc-shaped body piece 122, and having a not smooth texture on a peripheral surface 144 of first disc-shaped body piece 120 and potentially also upon a similar peripheral surface of second disc shaped body piece 122.

INDUSTRIAL APPLICABILITY

As discussed above, system 10 can be used in a variety of ways, and for therapeutic treatment of physical injuries or psychological/mental ailments. It is believed that multi-modal sensory stimulation directed at tactile stimulation with both smooth and not smooth textures, as well as heat, cold, or scent can impact user wellness in a manner not possible, or only in an inferior way, with known systems.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. For example, while the disclosed embodiments have body pieces that are disc-shaped, in other instances square, triangular, pyramidal, or even hemispheric body pieces could be used. Moreover, while a smooth texture is associated with outer domed surfaces of holders 14 and 114 with a not smooth texture being associated with peripheral surfaces of the respective body pieces, in other embodiments the peripheral surfaces might be smooth and the domed outer surfaces might be not smooth. Still other variations could include smooth and not smooth regions in an alternating pattern about the respective center axis upon either or both of the outer surfaces and the peripheral surfaces. Other aspects, features and advantages will be apparent upon an examination of the attached drawings and appended claims. As used herein, the articles "a" and "an" are intended to include one or more items, and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A personal therapy system comprising:
   a sensory stimulation pack including at least one of a heating device or a scent-emitting device;
   a holder including a holder body defining a center axis and having a first disc-shaped body piece, and a second disc-shaped body piece releasably attached to the first disc-shaped body piece;
   the first disc-shaped body piece and the second disc-shaped body piece each including a body wall having an outer peripheral wall, an inner surface, and an outer surface, and the inner surfaces forming a cavity receiving the sensory stimulation pack;

the first and second disc-shaped body pieces having a plurality of vents formed in the body walls thereof between the outer peripheral walls and the center axis, for outputting heat or scent from the cavity produced, respectively, by the at least one of a heating device or a scent-emitting device;

the outer surface of the first disc-shaped body piece forming a first outer touch surface having a smooth texture throughout and extending radially outward of, and circumferentially around, the center axis; and the first disc-shaped body piece outer peripheral wall depending axially downward from the body wall thereof, and including a peripheral surface forming a second outer touch surface, the second outer touch surface having a not smooth texture throughout which may be touched when the outer peripheral wall of the second disc-shaped body is received within the outer peripheral wall of the first disc-shaped body and extending, at a uniform radial distance, circumferentially around the center axis.

2. The system of claim 1 wherein the body wall of the first disc-shaped body piece has a dome shape.

3. The system of claim 2 wherein the plurality of vents each define a major axis extending radially outward of the center axis.

4. The system of claim 2 wherein at least one of the plurality of vents defines a major axis having a curvilinear path forming an arc segment about the center axis.

5. The system of claim 4 wherein the at least one of the plurality of vents has a curved teardrop shape.

6. The system of claim 2 wherein the body wall of the second disc-shaped body piece has a dome shape.

7. The system of claim 1 further comprising a twist lock releasably attaching the first disc-shaped body piece to the second disc-shaped body piece.

8. The system of claim 7 wherein:
the twist lock includes a first locking element formed on the first disc-shaped body piece and a second locking element formed on the second disc-shaped body piece; and
the first disc-shaped body piece and the second disc-shaped body piece being rotatable relative to one another about the center axis between a locking state, where the first locking element is in locking engagement with the second locking element, and a release state.

9. The system of claim 1 wherein each of the first disc-shaped body piece and the second disc-shaped body piece is formed of a molded polymeric material, and wherein the not smooth texture includes molded-in surface features of the second outer touch surface.

10. The system of claim 9 wherein the molded-in surface features include axially extending ribs, grooves, flutes, ridges, or scoring.

11. A personal therapy system comprising:
a sensory stimulation pack;
a holder including a holder body defining a center axis and having a first body piece, and a second body piece releasably attached to the first body piece;
the first body piece and the second body piece each including a body wall having an outer peripheral wall, an inner surface, and an outer surface, and the inner surfaces forming a cavity structured to receive the sensory stimulation pack;

the first body piece and the second body piece each having a plurality of vents formed in the body walls thereof between the outer peripheral wall and the center axis, for exposing a user to a sensory stimulation output of the sensory stimulation pack;

the outer surface of the first body piece forming a first outer touch surface having a first texture throughout and extending radially outward of, and circumferentially around, the center axis;

the first body piece outer peripheral wall depending axially downward from the body wall thereof and the second body piece outer peripheral wall depending axially upward from the body wall thereof and received within the first body piece outer peripheral wall; and the first body piece outer peripheral wall further including a peripheral surface forming a second outer touch surface, the second outer touch surface having a second texture throughout and extending around the center axis.

12. The system of claim 11 further comprising a lock releasably attaching the first body piece to the second body piece such that the sensory stimulation pack is captured within the cavity.

13. The system of claim 11 wherein the sensory stimulation pack includes a temperature stimulation device.

14. The system of claim 13 wherein the sensory stimulation pack includes a heating device and a scent-emitting device.

15. The system of claim 11 wherein each of the first body piece and the second body piece is domed and disc-shaped.

16. The system of claim 11 wherein the first texture includes a smooth texture, and the second texture includes a not smooth texture.

17. A personal therapy system comprising:
a holder including a holder body defining a center axis and having a first body piece, and a second body piece releasably attached to the first body piece;
the first body piece and the second body piece each including a body wall having an outer peripheral wall, an inner surface, and an outer surface, and the inner surfaces forming a cavity structured to receive a sensory stimulation pack including at least one of a heating device or a scent-emitting device;
the first body piece and the second body piece having a plurality of vents formed in the body walls thereof between the outer peripheral wall and the center axis, for exposing a user to a sensory stimulation output of the sensory stimulation pack;
the outer surface of the first body piece forming a first outer touch surface having a first texture and extending radially outward of, and circumferentially around, the center axis; and
the first body piece outer peripheral wall depending axially downward from the body wall thereof, and including a peripheral surface forming a second outer touch surface, the second outer touch surface having a second texture which may be touched when the outer peripheral wall of the second body piece is received within the outer peripheral wall of the first body piece and extending around the center axis.

18. The system of claim 17 further comprising a twist lock releasably attaching the first body piece to the second body piece, and wherein:
each of the first body piece and the second body piece is domed and disc-shaped.

* * * * *